United States Patent
Graham

(10) Patent No.: US 10,973,938 B1
(45) Date of Patent: Apr. 13, 2021

(54) INSERT FOR SPRAYER BOTTLE FOR OZONATING WATER

(71) Applicant: Robert V. Graham, Wentworth, SD (US)

(72) Inventor: Robert V. Graham, Wentworth, SD (US)

(73) Assignee: Professional Server Certification Corporation, Madison, SD (US)

( * ) Notice: Subject to any disclaimer, the term of this patent is extended or adjusted under 35 U.S.C. 154(b) by 0 days.

(21) Appl. No.: 17/129,196

(22) Filed: Dec. 21, 2020

(51) Int. Cl.
*A61L 2/18* (2006.01)
*C25B 1/13* (2006.01)
*A61L 2/03* (2006.01)

(52) U.S. Cl.
CPC .............. *A61L 2/183* (2013.01); *A61L 2/035* (2013.01); *C25B 1/13* (2013.01); *A61L 2202/11* (2013.01); *A61L 2202/16* (2013.01)

(58) Field of Classification Search
None
See application file for complete search history.

(56) References Cited

U.S. PATENT DOCUMENTS

| | | |
|---|---|---|
| 9,079,227 B2 | 7/2015 | Barnes |
| 9,540,259 B2 | 1/2017 | Lutz et al. |
| 9,636,715 B1 | 5/2017 | Barnes |
| 10,413,925 B2 | 9/2019 | Gonzalez et al. |
| 10,610,902 B1 | 4/2020 | Brook et al. |
| 2013/0277211 A1 | 10/2013 | Joshi et al. |
| 2016/0097132 A1 | 4/2016 | Joshi et al. |

FOREIGN PATENT DOCUMENTS

| | | |
|---|---|---|
| CN | 111214684 A | 6/2020 |
| CN | 211865528 U | 11/2020 |

(Continued)

OTHER PUBLICATIONS

"2020 new innovated Portable USB Electrolytic Ozone Generator active oxygen water", Alibaba.com, retrieved from: https://www.alibaba.com/product-detail/2020-new-innovated-Portable-USb-Electrolytic_1700000972371.html?spm=a2700.galleryofferlist.normal_offer.d_image.6e7e31fcPCwZUf, (Video Submission), retrieved on Dec. 21, 2020.

(Continued)

*Primary Examiner* — Kishor Mayekar
(74) *Attorney, Agent, or Firm* — Caesar Rivise, PC

(57) ABSTRACT

An apparatus that can be connected to a conventional sprayer bottle that permits the sprayer bottle to generate ozonated water to be used as a cleaning fluid. The apparatus includes an insert member that can be releasably inserted between the spray head and the bottle portion. An ozonator element is coupled to the insert member via an electrical cable and wherein the ozonator element is configured to be submerged within a liquid contained within the bottle portion. With the insert secured on the bottle portion, the dip tube of the spray head can be passed through the insert member and into the liquid in the bottle portion and the spray head is secured onto the insert member. Electrical energy is provided through insert member to the ozonator element to ozonate the liquid in the bottle for predetermined period of time after which the sprayer bottle contains an ozonated liquid for cleaning. After another predetermined period of time, the ozonator element is energized again to ensure ozonated liquid is always available.

19 Claims, 8 Drawing Sheets

(56) References Cited

FOREIGN PATENT DOCUMENTS

CN           211914361 U     11/2020
WO    WO 2013/154914     10/2013

OTHER PUBLICATIONS

"Timer Relay, DROK Time Delay Relay DC 5V 12V 24V Delay Controller Board Delay-off Cycle Timer 0.01s-9999mins Trigger Delay Switching Relay Module with LCD Display Support Micro USB 5V Power Supply", Amazon.com, retrieved from: https://www.amazon.com/gp/product/B07DFT2WDS/ref=ox_sc_act_title_1?smid=AFHAE9RJVUMB&psc=1, retrieved on Dec. 21, 2020.
"Electrolytic Ozone Generator", Alibaba.com, retrieved from: https://mac-verin.en.alibaba.com/, retrieved on Dec. 21, 2020.

INSERT FOR SPRAYER BOTTLE FOR OZONATING WATER

BACKGROUND OF THE INVENTION

The present invention relates to relates generally to cleaning products that generate ozonated water and, more particularly, to an assembly that can be inserted into conventional spraying bottles for producing ozonated water.

The use of ozone ($O_3$) in different forms for sanitization is well-known. As a gas, ozone can be used for destroying mold or allergens but must be carefully administered because those levels of gaseous ozone can also be toxic to small children, pets and plants. However, when used in water, such ozonated water can be used to safely disinfect items or surfaces; in fact, ozonated water can even be ingested safely; for example, ozonated water is used by campers to clean water by destroying bacteria and other undesired content therein.

Devices that generate ozone are known as "ozonizers". Conventional ozonizers typically utilize electricity, or exposure to ultraviolet radiation, to convert oxygen ($O_2$) to ozone ($O_3$). The following U.S. patent references show examples of devices utilizing ozonated water. U.S. Pat. No. 9,079,227 (Barnes); U.S. Pat. No. 9,636,715 (Barnes); U.S. Pat. No. 9,540,259 (Lutz, et al.); U.S. Pat. No. 10,610,902 (Brook, et al.); U.S. Patent Publication Nos. 2013/0277211 (Joshi, et al.), now abandoned; and 2016/0097132 (Joshi, et al.), now abandoned.

While the devices disclosed in the aforementioned publications may be generally suitable for their intended purposes, these devices do not provide for convenient method of converting a conventional spray bottle into spray bottle of ozonated water. Thus, there remains a need for an insert that can be easily connected to a conventional spray bottle for generating ozonated water to act as a cleaning fluid.

All references cited herein are incorporated herein by reference in their entireties.

BRIEF SUMMARY OF THE INVENTION

An apparatus for permitting a conventional spray bottle to generate ozonated liquid (e.g., water) to act as a cleaning agent, and wherein the conventional spray bottle has a spray head and bottle portion, is disclosed. The apparatus comprises: an insert member that can be releasably inserted between the spray head and the bottle portion; an ozonator element that is coupled to said insert member via an electrical cable and wherein said ozonator element is configured to be submerged within a liquid contained within the bottle portion; and wherein the insert member conveys electrical power to the ozonator element to activate the ozonator element to ozonate the liquid contained with the bottle portion.

A method of ozonating a liquid (e.g., water) in a conventional spray bottle having a spray head with a dip tube and a bottle portion is disclosed. The method comprises: providing an insert member having an internal passageway and wherein the insert member can be releasably inserted between the spray head and the bottle portion, and wherein the insert member further comprising an ozonator element that is coupled to the insert member via an electrical cable; submerging the ozonator element within the liquid contained within the bottle portion; inserting the dip tube through the insert member and into the bottle portion; releasably securing a first end of the insert member to an opening in the bottle portion and a second end, opposite the first end, of the insert member to the spray head; applying electrical power through the insert member to activate the ozonator element for a first predetermined period of time to ozonate the liquid in the bottle portion.

BRIEF DESCRIPTION OF SEVERAL VIEWS OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE PREFERRED EMBODIMENTS

Figure 1:
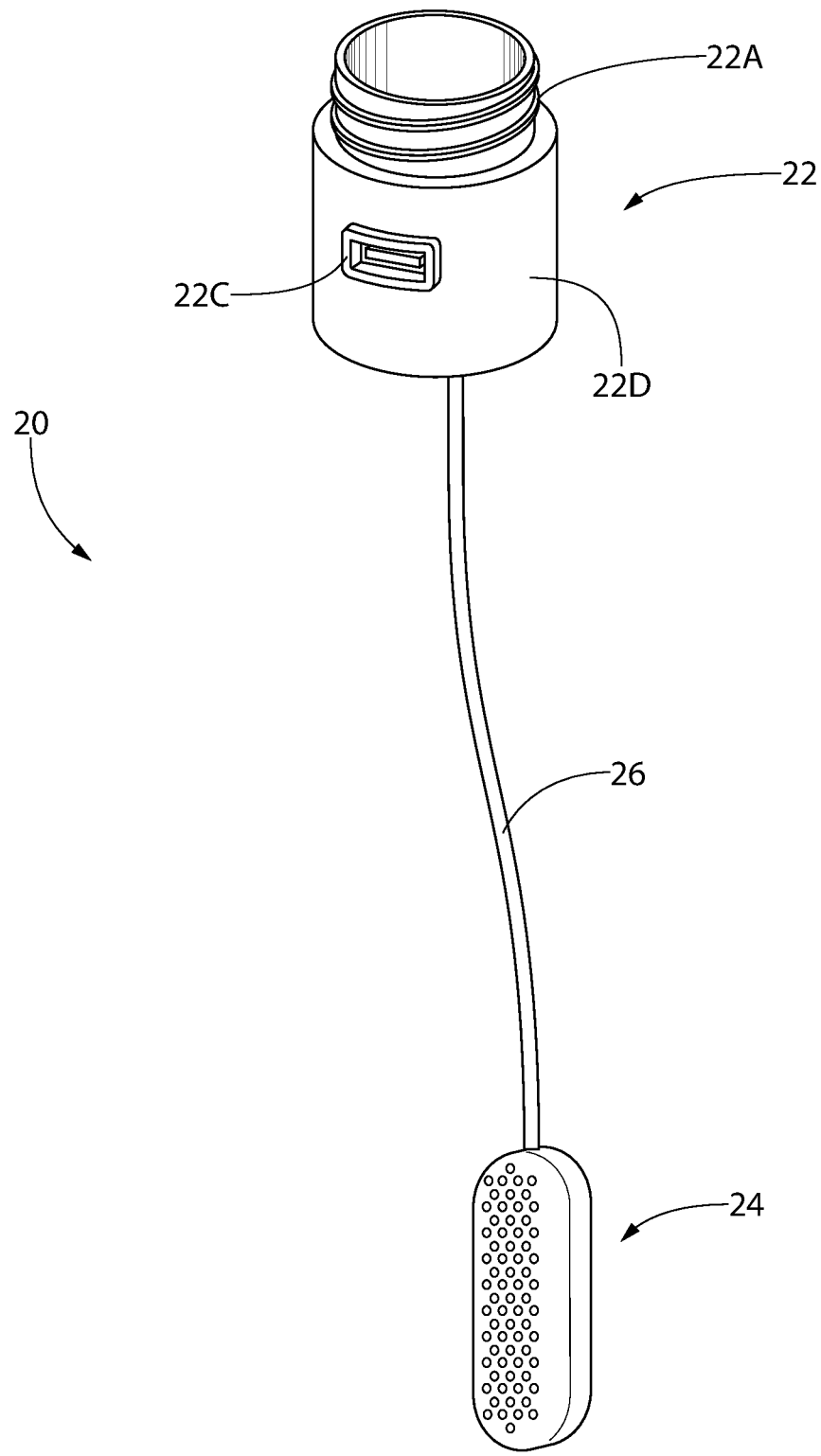
FIG. 1 depicts the insert assembly of the present invention.

Referring now to the figures, wherein like reference numerals represent like parts throughout the several views, exemplary embodiments of the present disclosure will be described in detail. Throughout this description, various components may be identified having specific values, these values are provided as exemplary embodiments and should not be limiting of various concepts of the present invention as many comparable sizes and/or values may be implemented.

Figure 2A:
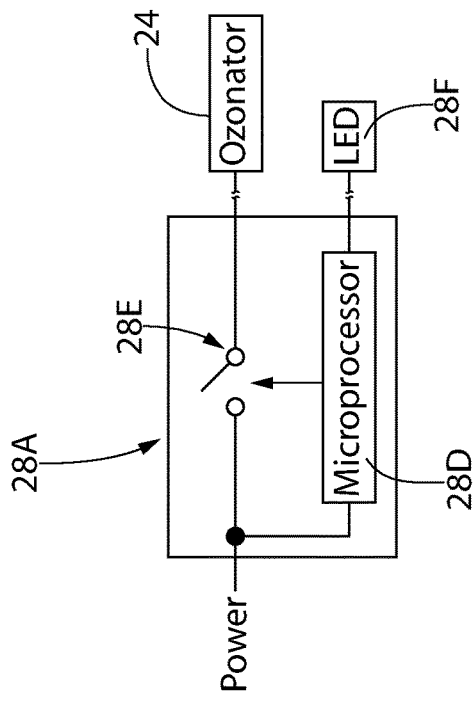
FIG. 2A is a schematic of the electronics of the present invention.
Figure 2:
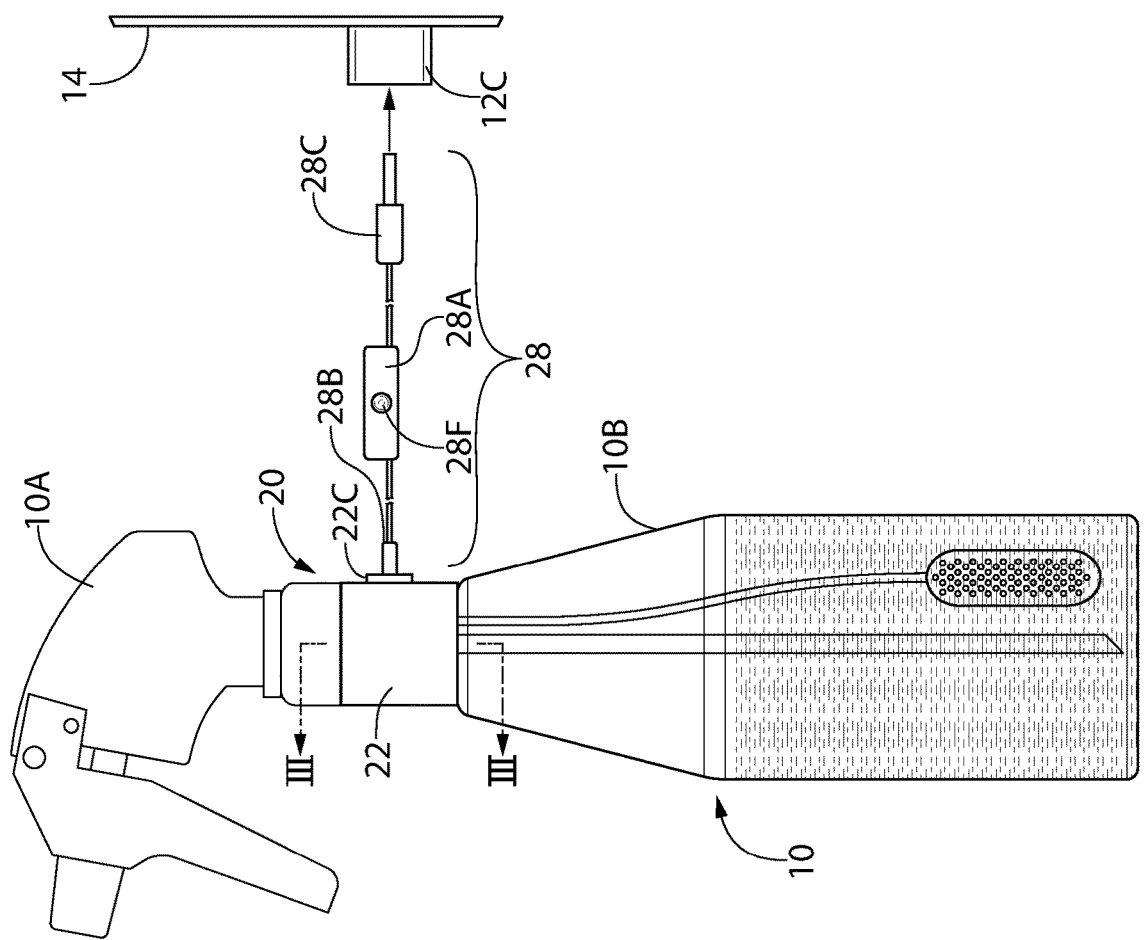
FIG. 2 depicts the insert assembly of the present invention installed in a conventional spray bottle with a power cord coupled to the insert for energizing the ozonator element.
Figure 3:
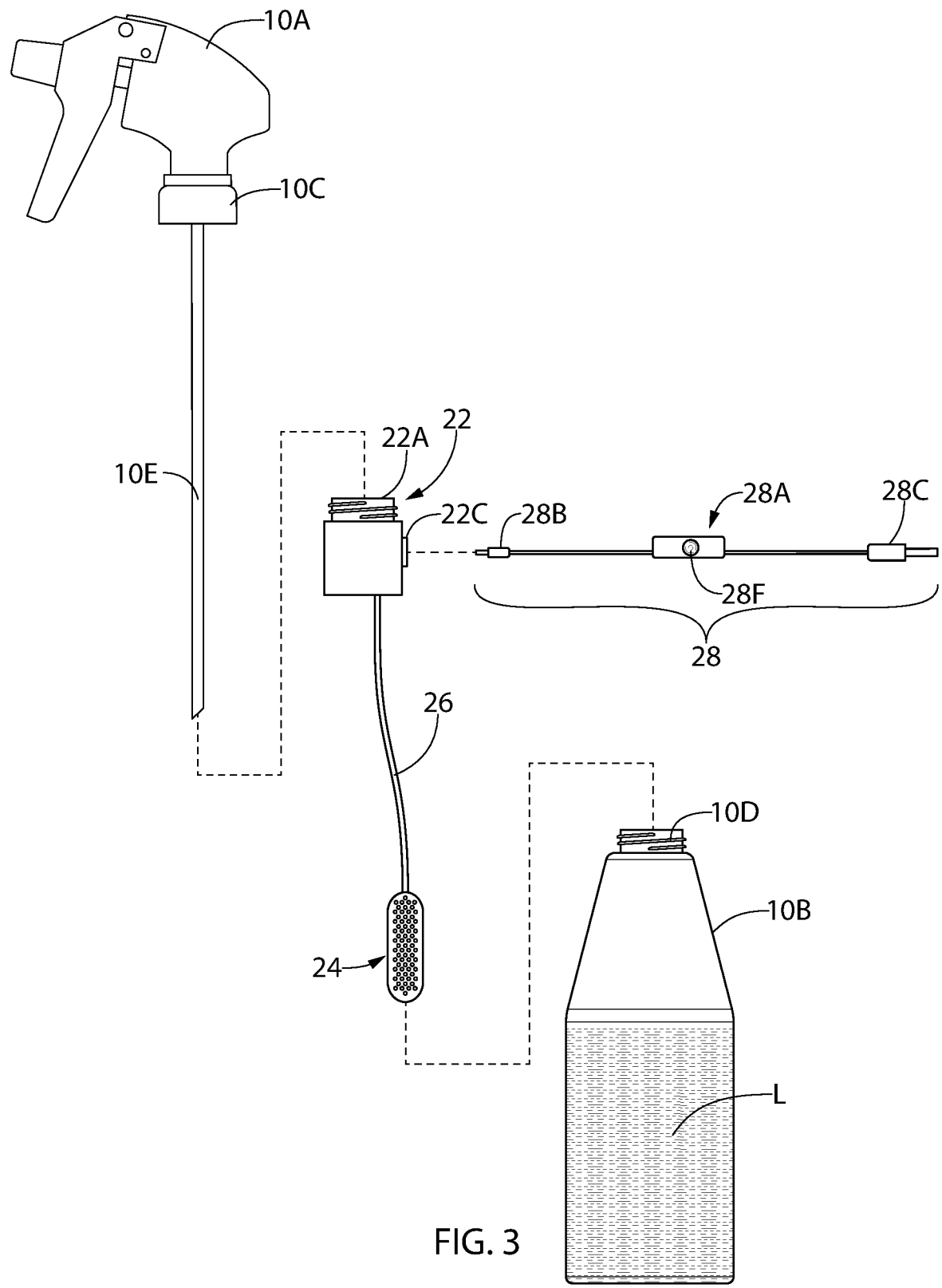
FIG. 3 is an exploded view of the present invention installed in a conventional spray bottle along with the power cord.

FIG. 1 depicts the insert assembly 20 of the present invention which comprises an insert member 22 and an ozonator element 24 (e.g., a portable electrolytic ozone generator such as the Moreclean Electrolyzed Ozone Generator sold by Alibaba.com) that is coupled to the insert member 22 via an electrical cable 26. The insert member 22 comprises an upper thread 22A (e.g., a threaded male connector) for engaging a corresponding threaded collar 10C in a spray head 10A of a conventional spray bottle 10 (FIGS. 2-3). The insert member 22 also comprises a lower thread 22B (e.g., a threaded female connector, see FIG. 3) for engaging a corresponding thread 10D on the top of a bottle portion 10B of the conventional spray bottle 10. The insert member 22 further comprises an electrical connector 22C (e.g., a USB receptacle) in a sidewall 22D of the insert member 22. To the internal side 22E of the electrical connector 22C is fixedly secured a first end of the electrical cable 26 for powering the ozonator element 24 coupled at the other end of electrical cable 26.

Figure 4:
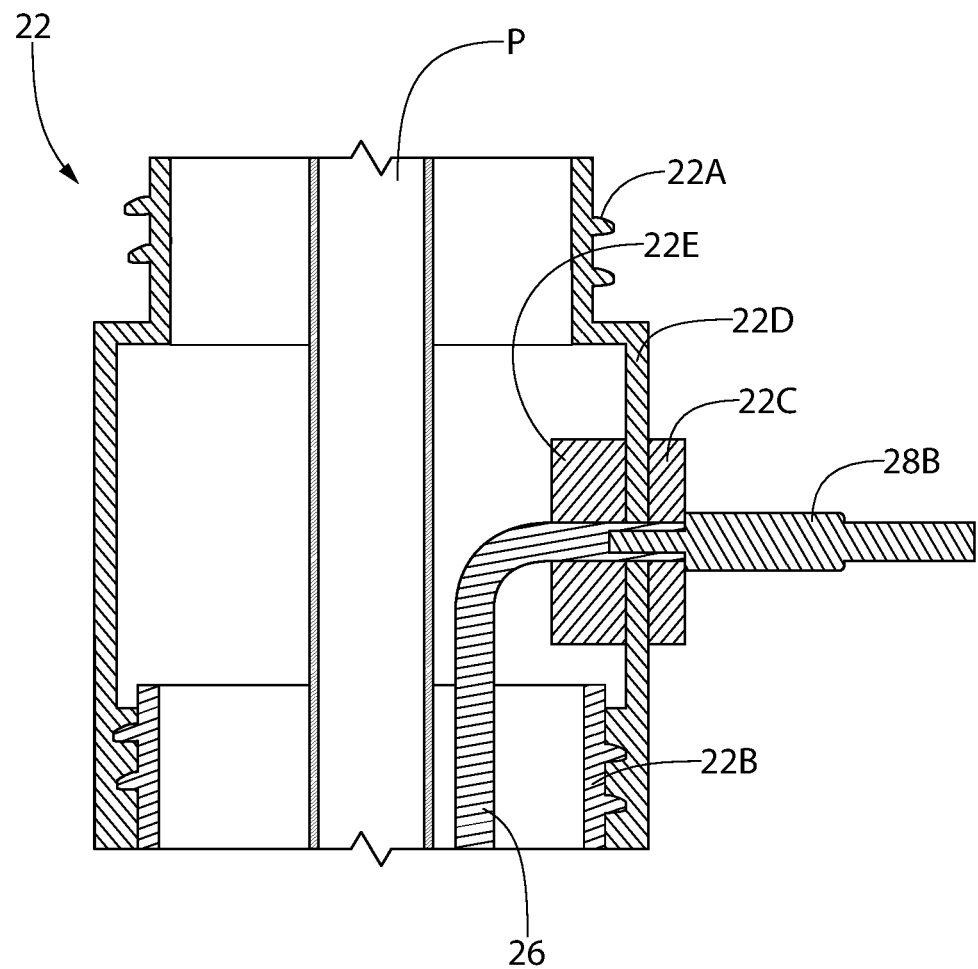
FIG. 4 is a cross-sectional view of the insert member taken along line III-III of FIG. 2.

As can be seen from FIG. 4, the insert member 22 basically forms a passageway P to allow the spray head dip tube 10E (FIG. 3) to easily pass therethrough and into the liquid L in the bottle portion 10B, as well as allowing the ozonator element 24 to be suspended inside the liquid L in the bottle portion 10B. (See FIG. 2). As such, the internal volume of the insert member 22 provides sufficient space or passageway for the dip tube 10E and the electrical cable 26 to pass easily into the opening to the bottle portion 10B. The insert member 22A may comprise a durable plastic material, e.g., PVC or ABS.

As mentioned previously, the ozonator element 24 may comprise a commercially-available portable electrolytic ozone generator. This ozonator element 24 draws very little electrical current and, as such, it is safe to use while it is submerged in the liquid L which is typically tap water. To ozonate the tap water in the bottle portion 10B, the ozonator element 24 need only be activated for a relatively short period of time, e.g., two minutes. This activation period (AP) may vary depending on the purity of the tap water. Once the ozonator element 24 is activated for the predetermined AP, the liquid L in the bottle portion 10B is "ozonated" and is ready for use as a cleaning or sanitizing agent. Once "ozonated", the liquid L in the bottle portion 10B will remain "ozonated" for approximately two hours. After that time, the ozonated state of the liquid L will return to its pre-ozonated state and will need to be "re-ozonated" to form a cleaning agent again. Although this "effective use period" (EUP) may vary, two hours is a reliable time for using the ozonated liquid as a cleaning agent before the liquid L requires re-ozonation.

One of the key aspects of the present invention 20 is to provide a "ready-to-use" ozonated cleaning product in a conventional spray bottle 10. This is accomplished by electronics associated with the insert assembly 20. In one embodiment, a power cord 28 is also provided that includes a controller 28A, a first USB connector 28B and a second USB connector 28C. The first USB connector 28B connects to the electrical connector 22C in the insert member 22 while the second USB connector 28C connects to a conventional USB wall plug converter 12 which is inserted into a conventional wall power outlet 14. As shown most clearly in FIG. 2A, the controller 28A comprises a microprocessor 28D (e.g., microcontroller such as Microchip ATTINY 4-MAHR etc.), a switch 28E (e.g., a solid-state switch, e.g., NPN, transistor, etc.) and an indicator 28F (e.g., a light-emitting diode (LED), e.g., a Cree Inc. C512A-WNN-CZ0B0151 LED).

Figure 5:
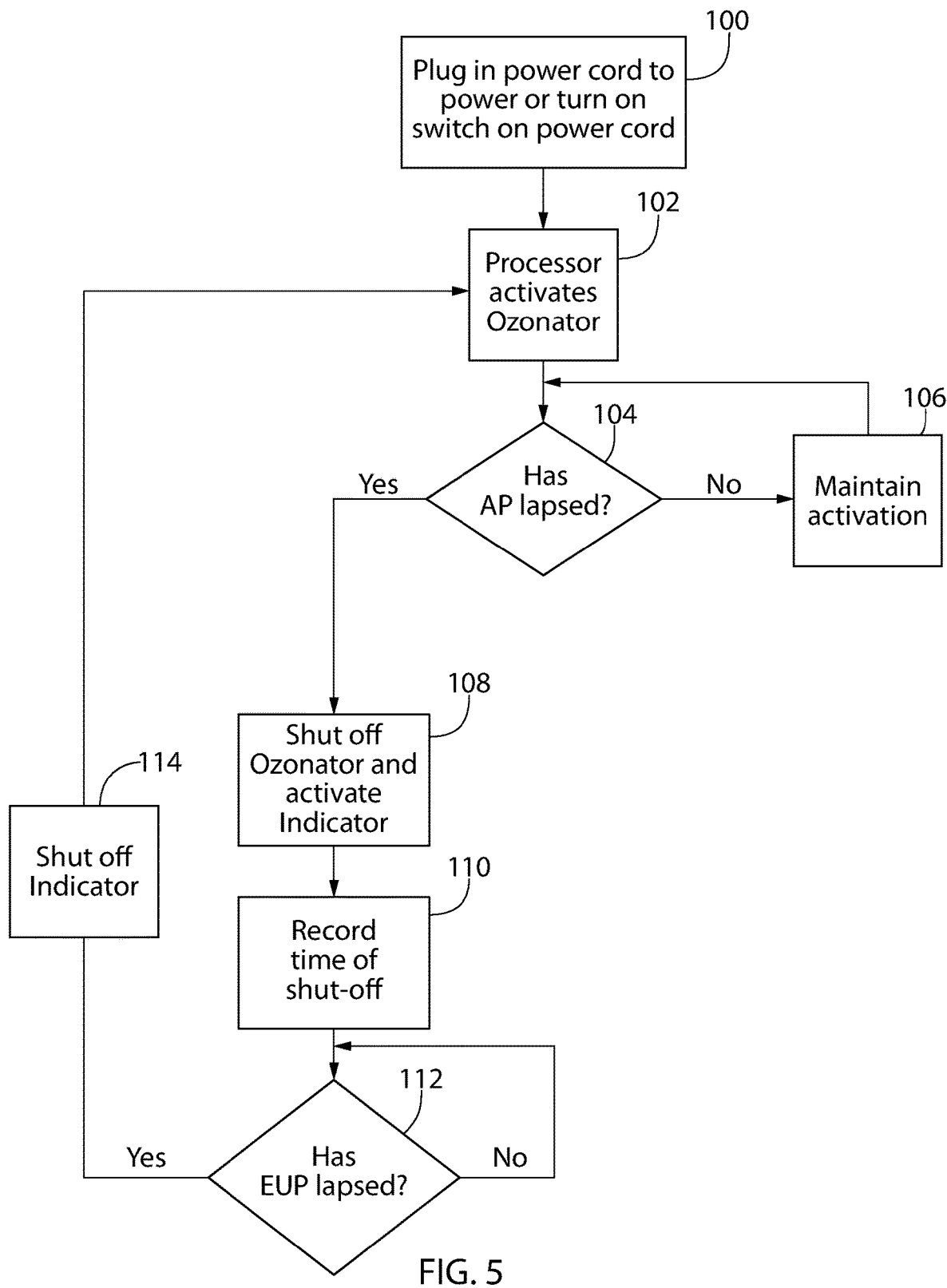
FIG. 5 is a flow diagram of the microprocessor operation in the electronics.

FIG. 5 depicts the microprocessor 28D operation with the bottle portion 10B filled and the insert assembly 20 installed and the spray head 10A installed. Once the power cord 28 is plugged into the connector 22C (step 100), the microprocessor 28D turns on the ozonator element 24 (step 102) and monitors the AP to determine if the AP has elapsed (step 104) or not (step 106). If the AP has elapsed, the microprocessor 28D shuts off the ozonator element 24 by opening the switch 28E and turns on the indicator 28F (step 108). The lighted indicator 28F lets the user know that he/she has a fully ozonated cleaning product ready for use. The microprocessor 28D notes the timestamp of the shut-off of the ozonator element 24 (step 110). The microprocessor 28D then monitors how much time has elapsed since the shut-off timestamp (step 112) to determine if the predetermined EUP has lapsed. If it has, the microprocessor 28D shuts of the indicator 28F (step 114) and immediately activates the ozonator element 24 (step 102) to re-ozonate the liquid L. As a result, this process guarantees that if a spray bottle 10 with the insert assembly 20 installed therein is plugged into wall power and no one has used the spray bottle, the liquid L is automatically re-ozonated after every EUP has lapsed.

Figure 5A:
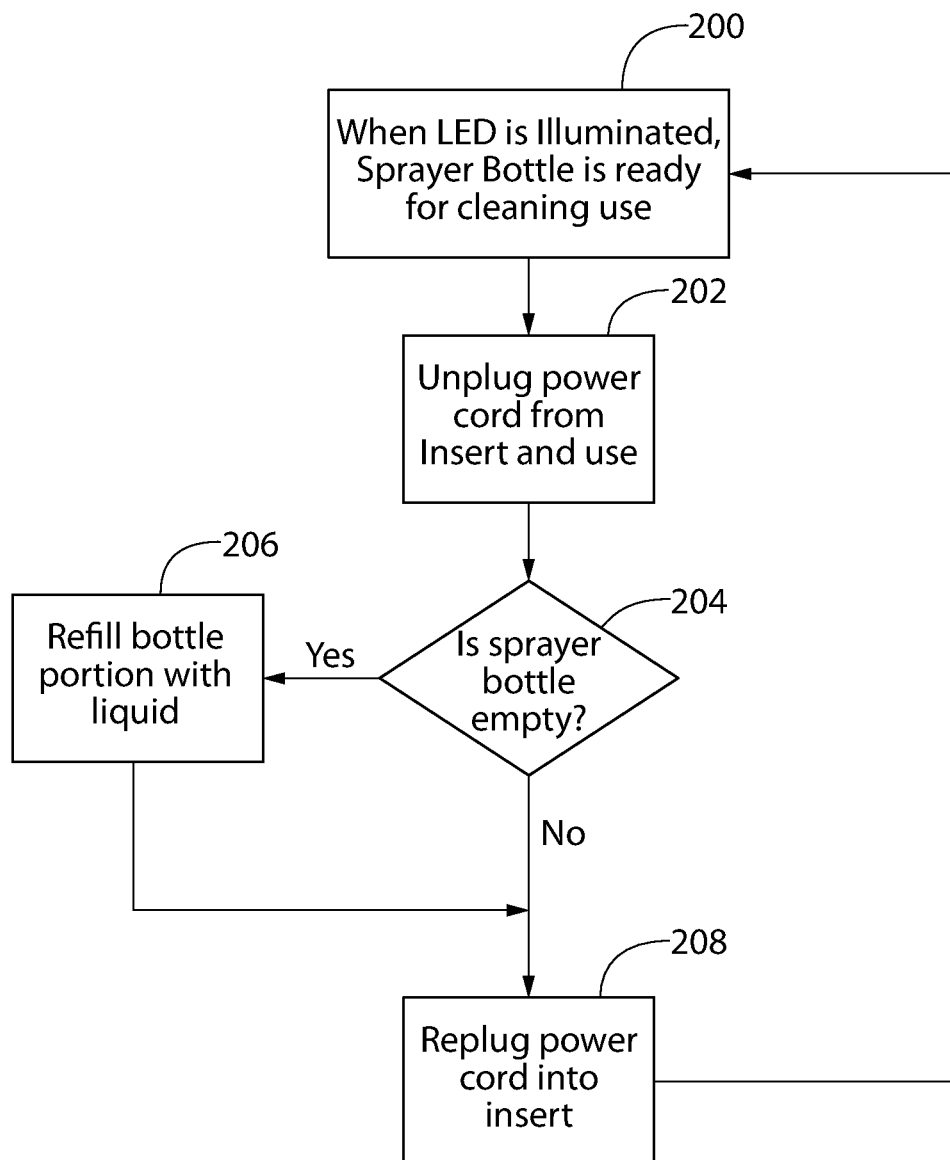
FIG. 5A is a flow diagram of the process of using the present invention in a conventional spray bottle.

FIG. 5A provides a flow diagram of the use of the spray bottle 10 with the insert assembly 20 installed therein and powered as describe above. With the indicator 28F illuminated (step 200), the user unplugs the power cord (step 202) by disengaging the USB connector 28B from the insert connector 22C. The user can now use the spray bottle 10 to clean. If the user empties the bottle portion 10B (step 204), the user will refill the bottle portion 10B (step 206) and then reconnect the power cord to the insert member 22 (step 208). Should the user not empty the bottle 10 and reconnects the power cord to the insert member 22, the microprocessor 28D will re-ozonate the remaining liquid L in the bottle portion 10B, even if the EUP has not lapsed; there is no concern in "re-ozonating" liquid L that is still within the EUP.

Figure 6:
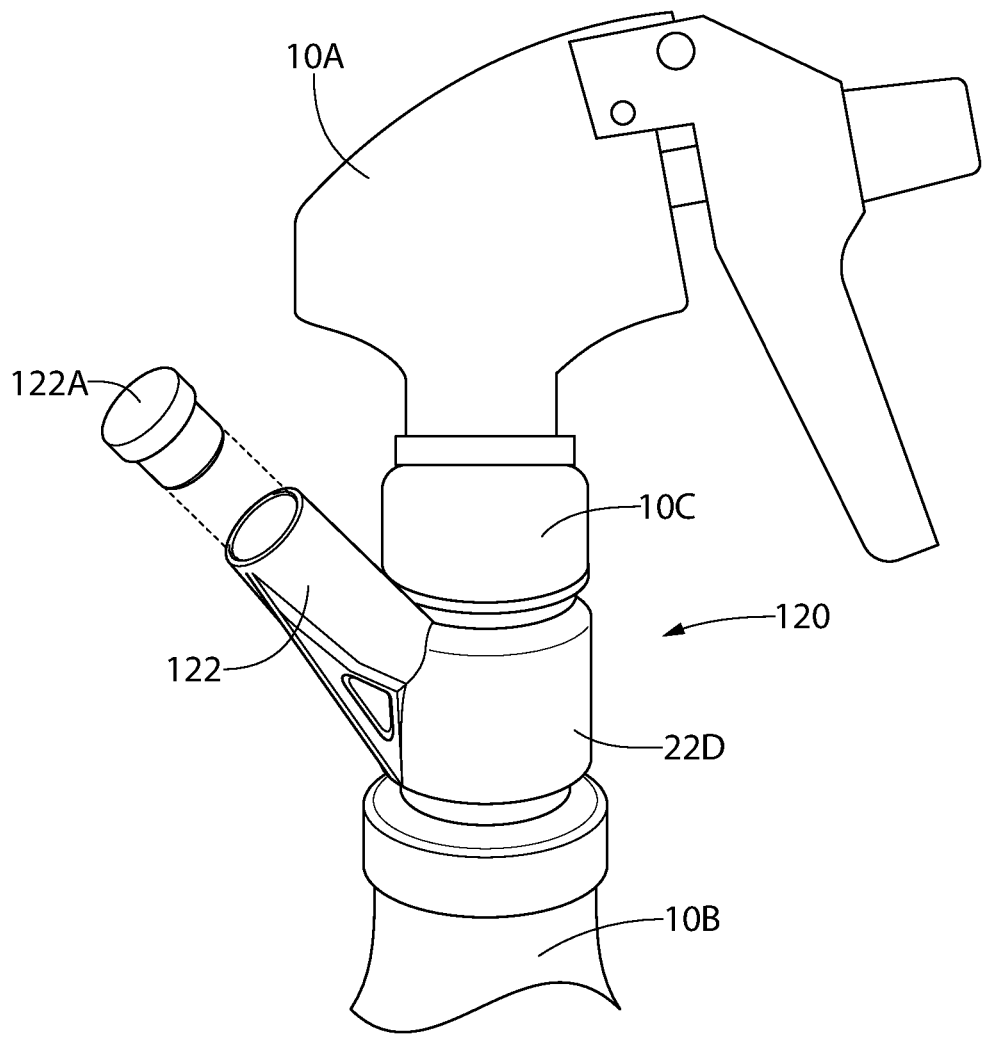
FIG. 6 is a partial view of an alternative insert member of the present invention which includes a spout and corresponding closure shown in an exploded condition.
Figure 7:
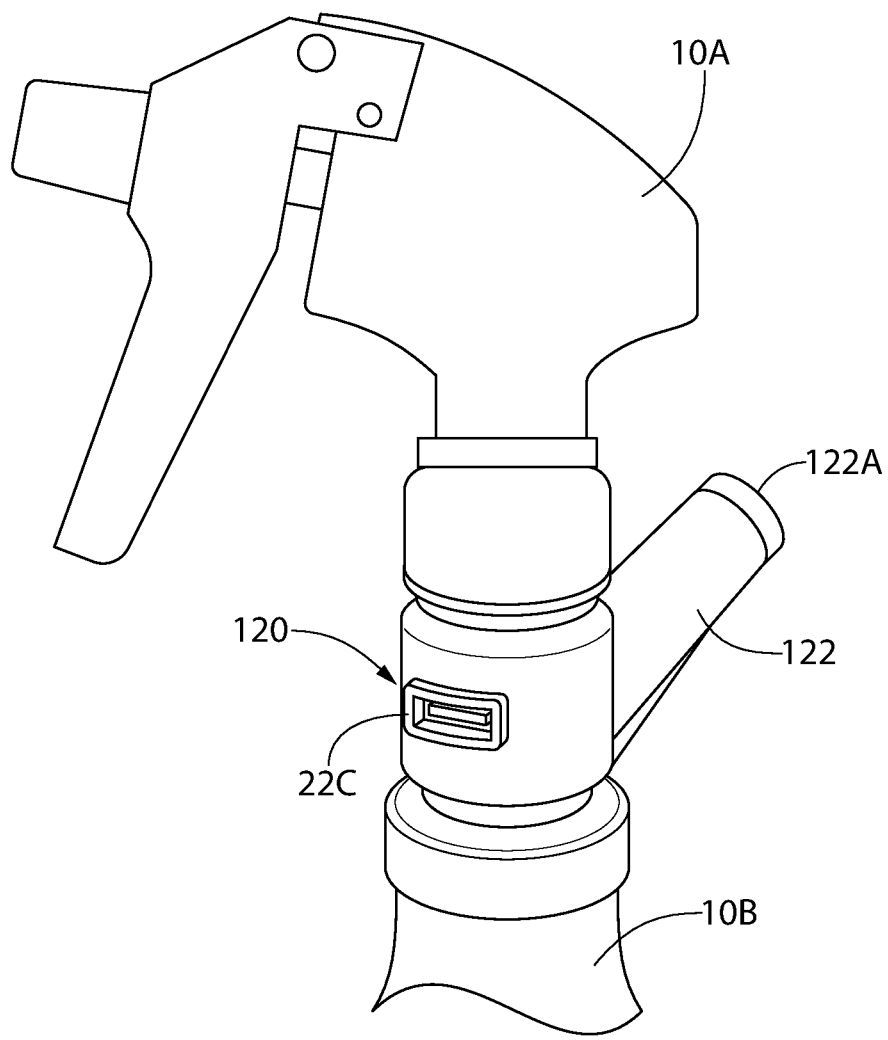
FIG. 7 is a partial back view of the alternative insert member of FIG. 6.

To make the use of the insert assembly even more convenient, an alternative insert assembly 120 is shown in FIGS. 6-7. The alternative insert assembly 120 is identical to the insert assembly 20 but includes a refill spout 122 with an associated removable closure 122A. As discussed above, when the ozonated liquid L is emptied from the bottle 10B in step 206, the user needs to refill the bottle portion 10B. Instead of having to disengage the spray head 10A or the insert assembly 22 from the bottle portion 10B, the user can simply remove the closure 122A (e.g., a cap), pour in more liquid L and then reinstall the closure 122A. The user then inserts the power cord 28 to the connector 22C in the insert member 120 and the process of FIG. 5 is carried out.

It should be noted that the use of USB connectors is simply by way of example and that it is within the broadest scope of the invention 20/120 to include all types of electrical connectors for powering the ozonator element 24 and controlling its energization. Furthermore, it is within the broadest scope of the invention to include the controller 28A on the insert member 22 itself, rather than in the power cord 28. Moreover, it is also within the broadest scope of the invention 20/120 to utilize a replaceable battery or a rechargeable battery on or within the insert assembly 20/120.

A key aspect to this invention 20/120 is that power to the ozonator element 24 is being provided from the insert member 22 either from an external power source (e.g., a wall outlet, etc.) or from an on-board power source (e.g., a replaceable battery or a rechargeable battery, etc.) associated with the insert member 20/120. Furthermore, where the controller 28A itself is located within or on the insert member 22, an exemplary module such the DROK Time Delay Relay DC 5V-12V-24V Delay Controller Board Delay-Off Cycle Timer board may be used.

It is also within the broadest scope of the present invention to include a user interface with the controller 28A that would permit the user to adjust the AP based on the purity of liquid (e.g., water) being used in the sprayer bottle 10, as well as being able to adjust the EUP to ensure that ozonated liquid is always present in the sprayer bottle 10.

While the invention has been described in detail and with reference to specific examples thereof, it will be apparent to one skilled in the art that various changes and modifications can be made therein without departing from the spirit and scope thereof.

What is claimed is:

1. An apparatus for permitting a conventional spray bottle to generate ozonated liquid to act as a cleaning agent, the conventional spray bottle having a spray head and bottle portion, said apparatus comprising:

an insert member that can be releasably inserted between the spray head and the bottle portion;

an ozonator element that is coupled to said insert member via an electrical cable and wherein said ozonator element is configured to be submerged within a liquid contained within the bottle portion; and wherein said insert member conveys electrical power to said ozonator element to activate said ozonator element to ozonate the liquid contained with the bottle portion.

2. The apparatus of claim 1 wherein said insert comprises a first threaded portion for releasably securing to the spray head and a second threaded portion for releasably securing to a top portion of the bottle portion.

3. The apparatus of claim 1 wherein said insert comprises an internal volume that permits a dip tube of the spray head to pass therethrough along with the electrical cable that is coupled between said electrical connector and said ozonator element.

4. The apparatus of claim 1 wherein said insert member comprises a sidewall having an electrical connector thereat, said electrical connector configured for receiving a power cord from an external power source for providing the electrical power to said ozonator element.

5. The apparatus of claim 4 further comprising a controller that provides the electrical power to said ozonator element for a predetermined activation period to form the ozonated liquid.

6. The apparatus of claim 5 further comprising an indictor coupled to said controller, said controller illuminating said indicator when said predetermined activation period is concluded.

7. The apparatus of claim 5 wherein said predetermined activation period is two minutes.

8. The apparatus of claim 5 wherein said controller tracks a time elapsed since said predetermined activation period has terminated, thereby defining an effective use period of said ozonated liquid, after which said controller applies electrical power to said ozonator element for said predetermined activation period.

9. The apparatus of claim 8 wherein said effective use period comprises two hours.

10. The apparatus of claim 1 wherein said insert member further comprises a spout with an associated closure, said spout permitting said bottle portion to be refilled with liquid without having to disengage said insert member from the bottle portion and without having to disengage the spray head from the bottle portion, said closure provided for closing off said spout once said bottle portion is refilled.

11. A method of ozonating a liquid in a conventional spray bottle having a spray head with a dip tube and a bottle portion, said method comprising:

providing an insert member having an internal passageway and wherein said insert member can be releasably inserted between the spray head and the bottle portion, said insert member further comprising an ozonator element that is coupled to said insert member via an electrical cable submerging said ozonator element within the liquid contained within the bottle portion;

inserting the dip tube through said insert member and into the bottle portion;

releasably securing a first end of said insert member to an opening in the bottle portion and a second end, opposite said first end, of said insert member to the spray head;

applying electrical power through said insert member to activate said ozonator element for a first predetermined period of time to ozonate the liquid in the bottle portion.

12. The method of claim 11 wherein said step of providing an insert member comprises forming a first threaded portion on said first end for releasably securing to the spray head and a forming second threaded portion on said second end for releasably securing to a top portion of the bottle portion.

13. The method of claim 11 wherein said insert member comprises a sidewall having an electrical connector thereat, and wherein said step of applying electrical power comprises coupling a power cord to said electrical connector, said power cord being electrically connected to an external power source for providing the electrical power to said ozonator element.

14. The method of claim 13 wherein said step of coupling the power cord comprises providing a controller that provides electrical power to said ozonator element for a predetermined activation period to form the ozonated liquid.

15. The method of claim 14 wherein said step of coupling the power cord comprises providing an indicator coupled to said controller wherein said controller illuminates said indicator when said predetermined activation period is concluded.

16. The method of claim 15 wherein said predetermined activation period is two minutes.

17. The method of claim 14 wherein said step of providing a controller further comprises said controller tracking a time elapsed since said predetermined activation period has terminated, thereby defining an effective use period of said ozonated liquid, after which said controller applies electrical power to said ozonator element for said predetermined activation period.

18. The method of claim 17 wherein said effective use period comprises two hours.

19. The method of claim 11 wherein said step of providing an insert member further comprises forming a spout with an associated closure in said insert member, said spout permitting said bottle portion to be refilled with liquid without having to disengage said insert member from the bottle portion and without having to disengage the spray head from the bottle portion, said closure provided for closing off said spout once said bottle portion is refilled.

* * * * *